United States Patent
Ham et al.

(10) Patent No.: US 6,914,159 B1
(45) Date of Patent: Jul. 5, 2005

(54) PROCESS FOR PREPARING SULFAMOYL-SUBSTITUTED PHENETHYLAMINE DERIVATIVES

(75) Inventors: Won Hun Ham, Seoul (KR); Chang Young Oh, Seoul (KR); Kee Young Lee, Kyunggi-do (KR); Yong Hyun Kim, Seoul (KR); Yiu Suk Lee, Seoul (KR)

(73) Assignee: Yonsung Fine Chemical Co., Ltd. (KR)

( * ) Notice: Subject to any disclaimer, the term of this patent is extended or adjusted under 35 U.S.C. 154(b) by 0 days.

(21) Appl. No.: 10/468,124

(22) PCT Filed: Feb. 7, 2002

(86) PCT No.: PCT/KR02/00199

§ 371 (c)(1),
(2), (4) Date: Aug. 15, 2003

(87) PCT Pub. No.: WO02/068382

PCT Pub. Date: Sep. 6, 2002

(30) Foreign Application Priority Data

Feb. 23, 2001 (KR) .................................. 2001-0009291

(51) Int. Cl.$^7$ .............................................. C07C 303/40
(52) U.S. Cl. ......................................................... 564/86
(58) Field of Search ........................................... 564/86

(56) References Cited

U.S. PATENT DOCUMENTS 4,971,990 A * 11/1990 Itoh et al. .................... 514/408
5,447,958 A    9/1995 Niigata et al. .............. 514/603

FOREIGN PATENT DOCUMENTS

| JP | 62-114952 A | 5/1987 |
| JP | 2-306958 A | 12/1990 |
| JP | 2000-229901 | 8/2000 |

* cited by examiner

Primary Examiner—Peter O'Sullivan
(74) Attorney, Agent, or Firm—Peter F. Corless; Christine C. O'Day; Edwards & Angell, LLP

(57) ABSTRACT

The present invention relates to a novel process for preparing sulfamoyl-substituted phenethylamine derivatives, specifically, 5-{2-[2-(2-alkoxy-phenoxy)ethylamino]-propyl}-2-methoxy-benzene sulfonamide of the formula (1).

12 Claims, No Drawings

PROCESS FOR PREPARING SULFAMOYL-SUBSTITUTED PHENETHYLAMINE DERIVATIVES

TECHNICAL FIELD

The present invention relates to a novel process for preparing sulfamoyl-substituted phenethylamine derivatives, specifically, 5-{2-[2-(2-alkoxy-phenoxy)ethylamino]-propyl}-2-methoxy-benzene sulfonamide of the following formula:

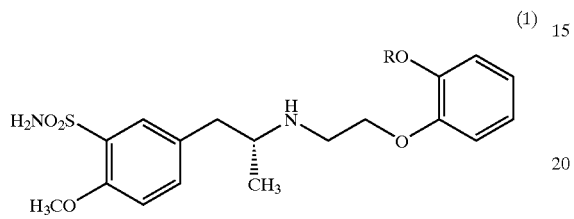

(1)

, wherein R represents $C_{1-4}$alkyl, or hydrochlorides thereof.

BACKGROUND ART

It is described in the U.S. Pat. No. 5,447,958 that the compounds of the above formula (1) have excellent therapeutic effects against hypertension, congestive heart failure, angina pectoris or prostatic hypertrophy. In addition, in the above patent, a process for preparing the compounds of the formula (1) by reacting hydrochlorides of the compounds of the following formula:

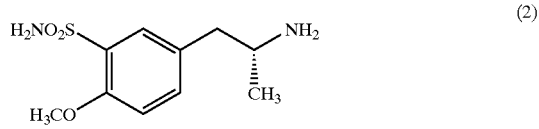

(2)

with the compounds of the following formula:

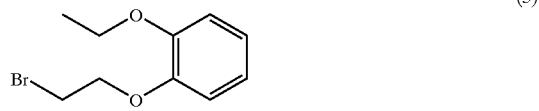

(3)

is disclosed. However, the above process has many drawbacks such as an extremely low yield (about 45%), a high production costs due to the purification by column chromatography and inapplicability in a large-scale production.

DISCLOSURE OF THE INVENTION

The present inventors have extensively studied to develop a novel preparation process in which the compounds of the formula (1) can be obtained in a high yield and can be easily purified. As a result, they found out that the preparation process of the compounds of the formula (I) by reacting compounds of the formula:

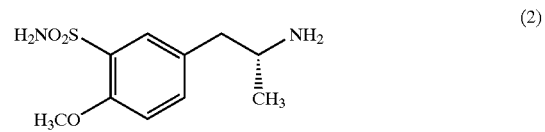

(2)

or hydrochlorides thereof with compounds of the formula:

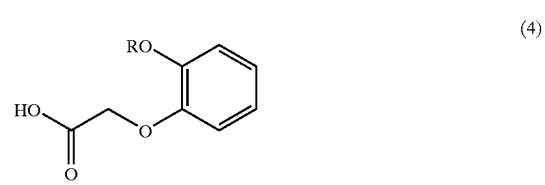

(4)

, wherein R represents $C_{1-4}$alkyl, or acid chlorides or mixed anhydrides thereof, in the presence of a base, in a reaction solvent to obtain the compounds of the formula:

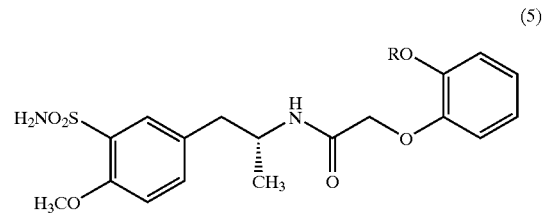

(5)

, wherein R is as defined above, and reducing the obtained compounds of the formula (5) with a reducing agent is not only economical but also efficient, because the compounds of the formula (1) can be obtained in a high yield, can be easily purified and can be prepared in a large scale, and completed the present invention.

Therefore, an object of the present invention is to provide a novel process for preparing sulfamoyl-substituted phenethylamine derivatives, specifically, compounds of the formula:

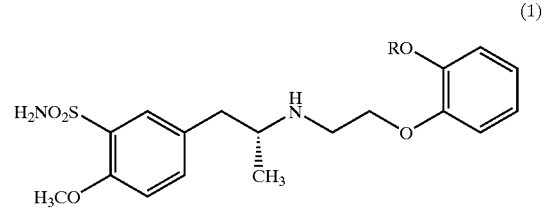

(1)

, wherein R represents $C_{1-4}$alkyl, or hydrochlorides thereof.

The present invention relates to a process for preparing the compounds of the formula:

(1)

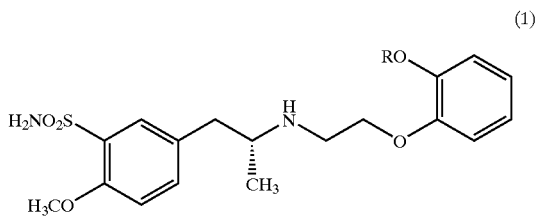

, wherein R represents $C_{1-4}$alkyl, or hydrochlorides thereof, which comprises (i) reacting compounds of the formula:

(2)

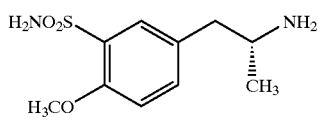

or hydrochlorides thereof with compounds of the formula:

(4)

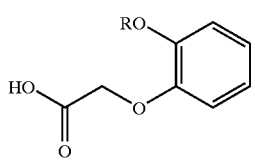

, wherein R is as defined above, or acid chlorides or mixed anhydrides thereof, in the presence of a base, in a reaction solvent to obtain compounds of the formula:

(5)

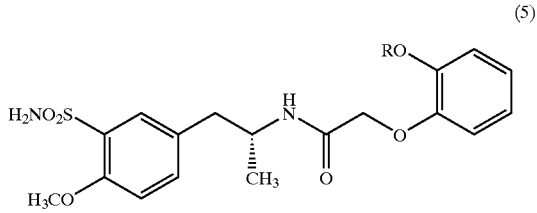

, wherein R is as defined above; and, (ii) reducing the obtained compounds of the formula (5) with a reducing agent.

The above reaction may be depicted by the following reaction scheme:

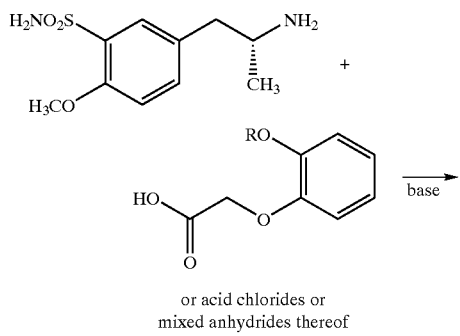

or acid chlorides or mixed anhydrides thereof

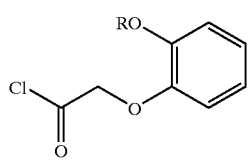

-continued

Hereinafter, the present invention will be specifically explained. The process according to the present invention comprises the following two steps.

1st Step: Preparation of Compounds of the Formula (5)

Compounds of the formula (5) are prepared by reacting compounds of the formula (2) or hydrochlorides thereof with compounds of the formula (4), or acid chlorides or mixed anhydrides thereof, in the presence of a base, in a reaction solvent. More specifically, the compounds of the formula (5) can be prepared by:

a) reacting compounds of the formula (2) or hydrochlorides thereof with acid chlorides of compounds of the formula (4);

b) reacting compounds of the formula (2) or hydrochlorides thereof with mixed anhydrides of compounds of the formula (4); or, c) reacting compounds of the formula (2) or hydrochlorides thereof with compounds of the formula (4).

In the above reaction, any conventional base such as trialkylamine, for example, trimethylamine, triethylamine or diisopropylethylamine, or inorganic bases, for example, $K_2CO_3$, $Na_2CO_3$, $KHCO_3$ or $NaHCO_3$, etc. may be employed and triethylamine is particularly preferable.

Acid chlorides of the compounds of the formula (4) employed in the process variant a) are represented by the following formula:

(4a)

, wherein R represents $C_{1-4}$alkyl, which can be prepared by reacting the compounds of the formula (4) with an acid chloride, for example, $SOCl_2$, $PCl_3$, $PCl_5$, $POCl_3$ or oxalyl chloride, etc. A reaction solvent employable in the above process variant a) may be any polar or non-polar solvent which does not affect the reaction. Dimethylformamide (DMF), dimethylsulfoxide (DMSO), dimethylacetamide (DMA) or tetrahydrofuran (THF), etc. is preferable and THF is particularly preferable. A reaction temperature ranging from about 0 to 100° C. is preferable.

Mixed anhydrides of the compounds of the formula (4) employed in the process variant b) are represented by the following formula:

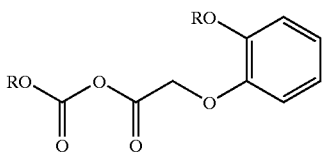 (4b)

, wherein R represents $C_{1-4}$alkyl and R' represents alkyl, allyl or aryl, which can be prepared by reacting the compounds of the formula (4) with compounds of the formula:

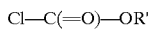 (4c)

, wherein R' is as defined above.

Preferable examples of the compounds of the formula (4c) include $C_{1-4}$alkylchloroformate such as methyl chloroformate, ethyl chloroformate or isobutyl chloroformate, phenyl chloroformate or allyl chloroformate, etc. A reaction solvent employable in the above process variant b) may be any polar or non-polar solvent which does not affect the reaction. DMF, DMSO, DMA or THF, etc. is preferable and THF is particularly preferable. A reaction temperature ranging from about −20 to 50° C. is preferable.

In the process variant c) wherein compounds of the formula (4) per se are employed, compounds of the formula (5) can be prepared by reacting compounds of the formula (2) or hydrochlorides thereof with compounds of the formula (4), in the presence of an acylating agent in addition to a base. Examples of the acylating agent employable in the above reaction include dicyclohexylcarbodiimide, diisopropylcarbodiimide, 1-[3-(dimethylamino)propyl]-3-ethylcarbodiimide, bis(2-oxo-3-oxazolidinyl)phosphinic chloride, benzotriazol-1-yloxy-tris(dimethylamino)phosphonium hexafluorophosphate, O-benzotriazol-1-yl-N,N,N',N'-tetramethyluronium hexafluorophosphate, or O-7-azabenzotriazol-1-yl-N,N,N',N'-tetramethyluronium hexafluoroborate, etc. Preferable is dicyclohexylcarbodiimide. A reaction solvent employable in the above process variant c) may be any polar or non-polar solvent which does not affect the reaction. DMF, DMSO, DMA or THF, etc. is preferable and DMF, DMSO or DMA is particularly preferable. A reaction temperature ranging from about 0 to 100° C. is preferable. Any additive, for example, dimethylaminopyridine, hydroxybenzotriazole or N-hydroxysuccinimide, etc. can be employed in the above process variant c). Such additive increases the reaction yield by suppression of side reactions.

In the first reaction step, an acylating agent, a base or an additive may be employed at a variable amount, preferably, at an amount of 1 to 3 equivalents, based on 1 equivalent of compounds of the formula (2) or hydrochlorides thereof. The reaction is performed while stirring for 1 to 24 hours. Then, the obtained compounds of the formula (5) are filtered, and the filtrate is concentrated under reduced pressure, extracted with ethyl acetate, washed, dried, filtered and concentrated under reduced pressure and then, employed in the subsequent reaction step.

2nd Step: Preparation of Compounds of the Formula (1)

Compounds of the formula (1) are prepared by reducing the compounds of the formula (5) obtained in the above first reaction step with a reducing agent in a reaction solvent. The reaction solvent employable in the above step may be any polar or non-polar solvent which does not affect the reaction. DMF, DMSO, DMA or THF, etc. is preferable and THF is particularly preferable. Examples of the reducing agent include lithium aluminum hydride, borane, diisobutylaluminum hydride, sodium borohydride-iodine or sodium borohydride-sulfate, etc. The reducing agent may be employed at an amount of about 2 to 6 equivalents. Preferably, a temperature of the reduction reaction ranges from about 40 to 80° C. and the reduction reaction is performed for 12 to 24 hours. Hydrochlorides of the compounds of the formula (1) can be obtained by addition of an anhydrous hydrochloric acid to the compounds of the formula (1).

The preparation process of the present invention is advantageous over the known process in that a higher yield can be obtained and the isolation step such as chromatography is not needed due to the easiness of purification.

BEST MODE FOR CARRYING OUT THE INVENTION

This invention will be better understood from the following examples. However, one skilled in the art will readily appreciate the specific materials and results described are merely illustrative of, and are not intended to, nor should be intended to, limit the invention as described more fully in the claims, which follow thereafter.

EXAMPLE 1

Synthesis of Compounds of the Formula (5) According to the Process Variant a)

1.30 g (11 mmol) of thionyl chloride was added to 1.96 g (10 mmol, 1.0 eq.) of (2-ethoxy-phenoxy)acetic acid. The mixture was heated under reflux for 30 minutes and distilled under reduced pressure to obtain (2-ethoxy-phenoxy)acetyl chloride. 20 ml of THF and 2.78 ml (20 mmol, 2.0 eq.) of triethylamine were added to 2.44 g (10 mmol, 1.0 eq.) of (R)-(-)-5-[(2-amino-2-methyl)ethyl]-2-methoxybenzene sulfonamide and the reaction solution was cooled down to 0° C. The obtained (2-ethoxy-phenoxy)acetyl chloride was added dropwise thereto and the whole mixture was stirred for 1 hour. The formed solids were filtered, and the filtrate was distilled under reduced pressure and extracted with 40 ml of ethyl acetate. Subsequently, the extract was washed with 1 N HCl, a saturated aqueous solution of sodium bicarbonate and brine, and dried over magnesium sulfate and then, filtered. The filtrate was distilled under reduced pressure to obtain 3.80 g (yield: 90%) of 2-(2-ethoxy-phenoxy)-N-[2-(4-methoxy-3-sulfamoyl-phenyl)-1-methyl-ethyl]-acetamide.

$^1$H NMR (CDCl$_3$, 500 MHz) 1.13 (d, 3H), 1.44 (t, 3H), 2.72 (dd, 1H), 2.85 (dd, 1H), 3.98 (s, 3H), 4.08 (m, 2H), 4.27 (m, 1H), 4.48 (dd, 2H), 5.06 (m, 3H), 6.87–7.02 (m, 5H), 7.34 (dd, 1H), 7.70 (d, 1H).

EXAMPLE 2

Synthesis of Compounds of the Formula (5) According to the Process Variant b)

20 ml of THF and 1.10 ml (10 mmol, 1.0 eq.) of N-methylmorpholine were added to 1.96 g (10 mmol, 1.0 eq.) of (2-ethoxy-phenoxy)acetic acid. The reaction solution was cooled down to 20° C. and 1.29 ml (10 mmol, 1.0 eq.) of isobutyl chloroformate was added thereto and the whole mixture was stirred for 30 minutes. 2.44 g (10 mmol, 1.0 eq.) of (R)-(-)-5-[(2-amino-2-methyl)ethyl]-2-methoxybenzene sulfonamide in a mixture of 20 ml of THF and 1.10 ml (10 mmol, 1.0 eq.) of N-methylmorpholine was slowly added thereto and the whole mixture was stirred for 4 hours. The formed solids were filtered and the filtrate was distilled under reduced pressure and extracted with 40 ml of ethyl acetate. Subsequently, the extract was washed with 1 N HCl, a saturated aqueous solution of sodium bicarbonate and brine, dried over magnesium sulfate and filtered. The filtrate was distilled under reduced pressure to obtain 3.84 g (yield: 91%) of 2-(2-ethoxy-phenoxy)-N-[2-(4-methoxy-3-sulfamoyl-phenyl)-1-methyl-ethyl]-acetamide.

NMR: as shown in the above example 1

EXAMPLE 3

Synthesis of Compounds of the Formula (5)
According to the Process Variant c)

50 ml of dimethylformamide was added to 2.44 g (10 mmol, 1.0 eq.) of (R)-(-)-5-[(2-amino-2-methyl)ethyl]-2-methoxybenzene sulfonamide and 1.96 g (10 mmol, 1.0 eq.) of (2-ethoxy-phenoxy)acetic acid and 1.35 g (10 mmol, 1.0 eq.) of hydroxybenzotriazole and 1.39 ml (10 mmol, 1.0 eq.) of triethylamine were sequentially added thereto and the reaction solution was cooled down to 0° C. 2.06 g (10 mmol, 1.0 eq.) of dicyclohexylcarbodiimide was added thereto and the reaction solution was warmed up to room temperature and then, stirred for 24 hours. The formed solids were filtered and the filtrate was concentrated under reduced pressure and extracted with 50 ml of ethyl acetate. Subsequently, the extract was sequentially washed with water, 10% hydrochloric acid and a saturated aqueous solution of sodium bicarbonate, dried over magnesium sulfate and filtered. The filtrate was concentrated under reduced pressure to obtain 4.01 g (yield: 95%) of 2-(2-ethoxy-phenoxy)-N-[2-(4-methoxy-3-sulfamoyl-phenyl)-1-methyl-ethyl]-acetamide.

NMR: as shown in the above example 1

EXAMPLE 4

Synthesis of Compounds of the Formula (5)
According to the Process Variant c)

50 ml of dimethylformamide, 5.23 ml (30 mmol, 3.0 eq.) of N,N-diisopropylethylamine, 4.42 g (10 mmol, 1.0 eq.) of benzotriazol-1-yloxy-tris(dimethylamino)phosphonium hexafluorophosphate were sequentially added to 2.44 g (10 mmol, 1.0 eq.) of (R)-(-)-5-[(2-amino-2-methyl)ethyl]-2-methoxybenzene sulfonamide and 1.96 g (10 mmol, 1.0 eq.) of (2-ethoxy-phenoxy)acetic acid and the mixture was stirred for 12 hours. Upon the completion of the reaction, the formed solids were filtered, and the filtrate was distilled under reduced pressure and extracted with 40 ml of ethyl acetate. Subsequently, the extract was washed with 1 N HCl, a saturated aqueous solution of sodium bicarbonate and brine, dried over magnesium sulfate and filtered. The filtrate was distilled under reduced pressure to obtain 4.05 g (yield: 96%) of 2-(2-ethoxy-phenoxy)-N-[2-(4-methoxy-3-sulfamoyl-phenyl)-1-methyl-ethyl]-acetamide.

NMR: as shown in the above example 1

EXAMPLE 5

Synthesis of Compounds of the Formula (1)

50 ml of tetrahydrofuran was added to 4.22 g (10 mmol, 1.0 eq.) of 2-(2-ethoxy-phenoxy)-N-[2-(4-methoxy-3-sulfamoyl-phenyl)-1-methyl-ethyl]-acetamide. 379 mg (10 mmol, 4.0 eq.) of lithium aluminum hydride was added thereto and the whole mixture was stirred at 60° C. for 24 hours. Upon the completion of the reaction, 0.4 ml of water, 0.4 ml of 10% NaOH aqueous solution and 1.2 ml of water were sequentially added to the reaction solution and then, filtered through celite. The filtrate was concentrated under reduced pressure to obtain 3.5 g of 5-{2-[2-(2-ethoxy-phenoxy)-ethylamino]-propyl}-2-methoxy-benzene sulfonamide. Thereto was added 10 ml of 2 M HCl solution in ethanol to obtain 3.56 g (yield: 80%) of 5-{2-[2-(2-ethoxy-phenoxy)-ethylamino]-propyl}-2-methoxy-benzene sulfonamide hydrochloride.

$[\alpha]^D_{20}$ 4.0 (c=0.35, methanol)

$^1$H NMR (DMSO-$d_6$, 500 MHz) 1.13 (d, 3H), 1.24 (t, 3H), 2.67 (dd, 1H), 3.27 (dd, 1H), 3.39 (m, 2H), 3.52 (m, 1H), 3.87 (s, 3H), 4.00 (q, 2H), 4.28 (t, 2H), 6.87–7.00 (m, 4H), 7.17 (s, 2H), 7.06–7.62 (m, 3H), 9.22 (s, 2H).

INDUSTRIAL APPLICABILITY

According to the preparation process of the present invention, the sulfamoyl-substituted phenethylamine derivatives can be economically and efficiently prepared in a large scale, because a high yield can be obtained and purification can be performed without any isolation such as chromatography.

What is claimed is:

1. A process for preparing the compounds of the formula:

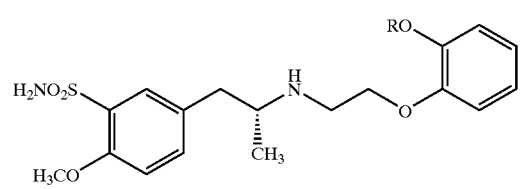
(1)

, wherein R represents $C_{1-4}$alkyl, or hydrochlorides thereof, which comprises
(i) reacting compounds of the formula:

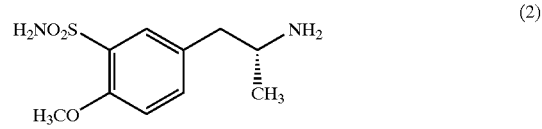
(2)

or hydrochlorides thereof with compounds of the formula:

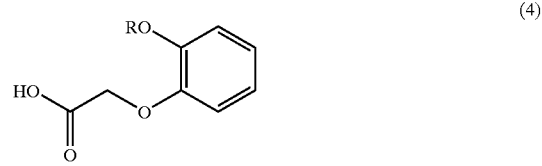
(4)

, wherein R is as defined above, or acid chlorides or mixed anhydrides thereof, in the presence of a base, in a reaction solvent to obtain compounds of the formula:

(5)

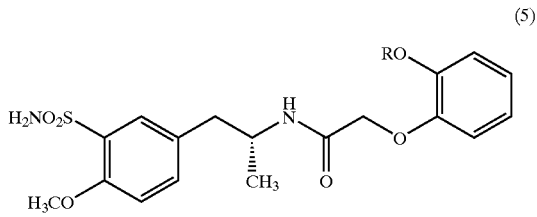

, wherein R is as defined above; and, (ii) reducing the obtained compounds of the formula (5) with a reducing agent.

2. The process of claim 1, wherein the acid chlorides of the compounds of the formula (4) are represented by the formula:

(4a)

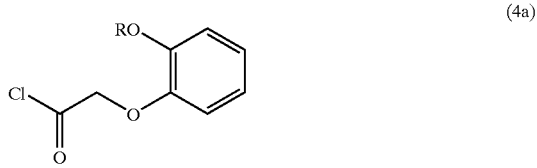

, wherein R represents $C_{1-4}$alkyl.

3. The process of claim 2, wherein the compounds of the formula (4a) are prepared by reacting the compounds of the formula (4) with an acid chloride selected from the group consisting of $SOCl_2$, $PCl_3$, $PCl_5$, $POCl_3$ and oxalyl chloride.

4. The process of claim 1, wherein the mixed anhydrides of the compounds of the formula (4) are represented by the formula:

(4b)

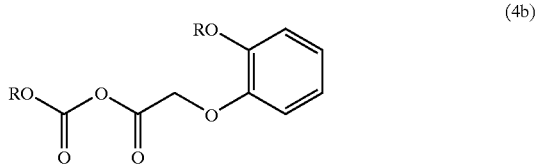

, wherein R represents $C_{1-4}$alkyl and R' represents alkyl, allyl or aryl.

5. The process of claim 4, wherein the compounds of the formula (4b) are prepared by reacting the compounds of the formula (4) with the compounds of the formula:

(4c)

wherein R' is alkyl, allyl or aryl.

6. The process of claim 5, wherein R' is methyl, isobutyl or phenyl.

7. The process of claim 1, wherein the compounds of the formula (2) or hydrochlorides thereof are reacted with the compounds of the formula (4), in the presence of an acylating agent in addition to the base to obtain the compounds of the formula (5) and the obtained compounds of the formula (5) are reduced with the reducing agent to obtain the compounds of the formula (1) or hydrochlorides thereof.

8. The process of claim 7, wherein the acylating agent is dicyclohexylcarbodiimide, diisopropylcarbodiimide, 1-[3-(dimethylamino)propyl]-3-ethylcarbodiimide, bis(2-oxo-3-oxazolidinyl)phosphinic chloride, benzotriazol-1-yloxy-tris (dimethylamino)phosphonium hexafluorophosphate, O-benzotriazol-1-yl-N,N,N',N'-tetramethyluronium hexafluorophosphate or O-7-azabenzotriazol-1-yl-N,N,N', N'-tetramethyluronium hexafluoroborate.

9. The process of any one of claims 1 to 8, wherein the base is trialkylamine or inorganic base.

10. The process of claim 9, wherein the trialkylamine is trimethylamine, triethylamine or diisopropylamine.

11. The process of any one of claims 1 to 8, wherein the reaction solvent is dimethylformamide (DMF), dimethylsulfoxide (DMSO), dimethylacetamide (DMA) or tetrahydrofuran (THF).

12. The process of any one of claims 1 to 8, wherein the reducing agent is lithium aluminum hydride, borane, diisobutylaluminum hydride, sodium borohydride-iodine or sodium borohydride-sulfate.

\* \* \* \* \*